United States Patent [19]

Papahadjopoulos

[11] 4,078,052
[45] Mar. 7, 1978

[54] LARGE UNILAMELLAR VESICLES (LUV) AND METHOD OF PREPARING SAME

[75] Inventor: P. Demetrios Papahadjopoulos, Buffalo, N.Y.

[73] Assignee: The United States of America as represented by the Secretary of Health, Education and Welfare, Washington, D.C.

[21] Appl. No.: 701,190

[22] Filed: Jun. 30, 1976

[51] Int. Cl.$^2$ .............................................. A61K 9/64
[52] U.S. Cl. .................................... 424/36; 252/316; 424/93; 424/359
[58] Field of Search ................ 252/316; 424/36, 359, 424/199

[56] References Cited

U.S. PATENT DOCUMENTS

| 3,069,370 | 12/1962 | Jensen et al. | 252/316 X |
| 3,607,776 | 9/1971 | Santo et al. | 252/316 |
| 3,692,899 | 9/1972 | Levy | 424/180 |

FOREIGN PATENT DOCUMENTS

| 2,249,552 | 5/1973 | Germany | 252/316 |

OTHER PUBLICATIONS

Hackh's Chemical Dictionary, 4th Edition, 1969, pp. 230 & 231.
Papahadjopoulos et al.: Cochleate Lipid Cylinders: Formation by Fusion of Unilamellar Lipid Vesicles, Biochim. Biophys. Acta., 394: 483–491, (1975).
Papahadjopoulos et al.,: Cellular Uptake of Cyclic AMP Captured within Phospholipid Vesicles and Effect on Cell-Growth Behaviour, Biochim. Biophys. Acta., 363: 404–418, (1974).
The Condensed Chemical Dictionary, 8th Edition, Revised by Hawley, Van Nostrand Reinhold Co., (1971), pp. 16, 75, 330, 764.

Primary Examiner—Richard D. Lovering
Attorney, Agent, or Firm—John S. Roberts, Jr.; Norman J. Latker; Thomas G. Ferris

[57] ABSTRACT

A process and resulting product for producing large unilamellar phosphatidylserine vesicles (LUV) in the diameter of about 2,000–12,000 Å which may additionally encapsulate a drug. The large vesicles are prepared from an initial phosphatidylserine aqueous solution which is subjected to ultrasound or sonicated which produces small unilamellar vesicles (SUV) in the diameter range of 200–500 Å. After the addition of calcium ion ($Ca^{2+}$) in the molar concentration of about 1–10 mM (threshold 1-2 mM) and incubating for 30–60 minutes at room temperature above 10° C and preferably 37° C, intermediate cochleate lipid cylinders form. Finally, addition of a calcium chelating agent such as EDTA or EGTA to these cochleate cylinders produces by fusion the desired large closed spherical unilamellar vesicles (LUV). The intermediate cochleate form appears specific to the phospholipid serine utilized and to the calcium ion ($Ca^{2+}$) incubating agent. Specific examples of drugs encapsulated in the phosphatidylserine LUV vesicles are Actinomycin D, cyclic 3'5'-adenosine monophosphate, Poly I Poly C, RNA, DNA, and arabinose cytocine and its phosphorylated analogs.

17 Claims, 4 Drawing Figures

LARGE UNILAMELLAR VESICLES (LUV) AND METHOD OF PREPARING SAME

The present invention relates to a process and resulting product for producing large unilamellar phosphatidylserine vesicles (LUV) in the diameter of about 2,000–12,000 A which may additionally encapsulate a drug. The large vesicles are prepared from an initial phsophatidylserine aqueous solution which is subjected to ultrasound or sonicated which produces small unilamellar vesicles (SUV) in the diameter range of 200–500 A. After the addition of calcium ion ($Ca^{2+}$) in the molar concentration of about 1–10 mM (threshold 1–2 mM) and incubating for 30–60 minutes at room temperature above 10° C and preferably 37° C, intermediate cochleate lipid cylinders form. Finally, addition of a calcium chelating agent such as EDTA or EGTA to these cochleate cylinders produces by fusion the desired large closed spherical unilamellar vesicles (LUV). The intermediate cochleate form appears specific to the phospholipid serine utilized and to the calcium ion ($Ca^{2+}$) incubating agent. Specific examples of drugs encapsulated in the phosphatidylserine LUV vesicles are Actinomycin D, cyclic 3'5'-adenosine monophosphate, Poly I Poly C, RNA, DNA, and arabinose cytocine and its phosphorylated analogs.

PRIOR ART (1) A. D. Bangham, M. M. Standish, and J. C. Watkins, "Diffusion of Univalent Ions Across the Lamellae of Swollen Phospholipids," *J. Mol. Biol.* 13:238–252, 1965.

(2) D. Papahadjopoulos and N. Miller, "Phospholipid Model Membranes. I. Structural Characteristics of Hydrated Liquid Crystals," *Biochim. Biophys. Acta,* 135:624–638, 1967.

(3) D. Papahadjopoulos, G. Poste, and E. Mayhew, "Cellular Uptake of Cyclic AMP Captured Within Phospholipid Vesicles and Effect on Cell-Growth Behaviour," *Biochim. Biophys. Acta,* 363:404–418, 1974.

(4) D. Papahadjopoulos, E. Mayhew, G. Poste, and S. Smith, "Incorporation of Lipid Vesicles by Mammalian Cells Provides a Potential Method for Modifying Cell Behaviour," *Nature,* 252:163–166, Nov, 8, 1974.

(5) D. Papahadjopoulos, W. J. Vail, K. Jacobson, and G. Poste, "Cochleate Lipid Cylinders: Formation by Fusion of Unilamellar Lipid Vesicles," *Biochim. Biophys. Acta,* 394:483–491, 1975.

(6) G. Poste and D. Papahadjopoulos, "Lipid Vesicles as Carriers for Introducing Materials into Cultured Cells," *Proc. Natl. Acad. Sci.,* 73:1603–1607, May 1976.

(7) George Poste and D. Papahadjopoulos, "Drug-Containing Lipid Vesicles Render Drug-Resistant Tumor Cells Sensitive to Actinomycin D, "*Nature,* In Press 1976.

(8) D. Papahadjopoulos, G. Poste, W. J. Vail, and J. L. Biedler, "Use of Lipid Vesicles as Carriers to Introduce Actinomycin D into Resistant Tumor Cells," *Cancer Research,* In Press 1976.

(9) D. Papahadjopoulos, W. J. Vail, W. A. Pangborn, and G. Poste, "Studies on Membrane Fusion. II. Induction of Fusion in Pure Phospholipid Membranes by $Ca^{2+}$ and Other Divalent Metals," *Biochim. Biophys. Acta,* In Press 1976.

(10) E. Mayhew, D. Papahadjopoulos et al, "Cellular Uptake and Protection Against Virus Infection by Poly I Poly C Entrapped Within Phospholipid Vesicles," submitted for publication 1976.

(11) French Pat. No. 2,221,122 — The patentee describes pellicles where the maximum diameter is 1,000 A similar to the present invention description of SUV. At pages 1–2 is described the encapsulation of medicaments or active cosmetic substances post an ultrasound treatment, for example theophilline (Example 1), insulin (Example 2), trypsin (Example 3), are encapsulated in a small phospholipid pellicle or liposome of 200–800 A and the maximum of 1,000 A. The procedures outlined in this French patent at pages 1 and 2 are essentially those previously described by the present investigators and reported in *Biochim. Biophys. Acta,* 135:624–638, 1967. These procedures have been used subsequently in many laboratories for the production of small unilamellar vesicles by ultrasonication. The ultrasonication is the first step of the present procedure leading to the formation of the large unilamellar vesicles (2,000–12,000 A). The essential new step in the procedure of the present invention involves incubation of the small vesicles in the presence of calcium (threshold 1–2 mM) which induces fusion of the vesicles to form cochleate cylinders. Following this, surplus calcium is chelated by addition of a calcium chelating agent such as EDTA and pH 7.4, which results in formation of large unilamellar vesicles (2,000–12,000 A). Additionally, in the present procedure, the internal aqueous space of the large unilamellar vesicles (LUV) can be used for encapsulation of large macromolecules which would not fit inside the small vesicles. Finally, the addition of calcium after sonication avoids any difficulty of ultrasound treatment as affecting labile biologically active compounds to be encapsulated.

The present inventionl relates to a method and resulting product obtained initially from an aqueous solution of phosphatidylserine. This phospholipid uniquely produces an intermediate cochleate structure fashion. Other phospholipids which do not cochleate but fuse directly to large particles in the presence of calcium ($Ca^{2+}$) include dipalmitoyl phosphatidyl glycerol (DPPG), dimyristoyl phosphatidyl glycerol (DMPG), phosphatidyl ethanolamine, phosphatidic acid, and phosphatidyl inositol. Thus, phosphatidylserine is specific to a series of geometrical form changes necessary to the production of a large unilamellar vesicle product with an intermediate cochleate form.

Initially in the present procedure, an aqueous solution of phosphatidylserine is treated in a bath-type sonicator utilizing a buffer solution of 100 mM NaCl. The ultrasound sonicating procedure may be utilized for a period of about 30 minutes to one hour. In a specific example, the sonicated dispersion of phosphatidylserine was centrifuged at 100,000 × g for one hour at 20° C. After sonication, small (200-500 A diameter) spherical vesicles were obtained which have been termed SUV, representing the term small unilamellar vesicles.

$Ca^{2+}$ ion in the form of a soluble salt such as calcium chloride was then used to produce the larger particles. Specifically $Ca^{2+}$ was added to the sonicated phosphatidylserine preparation at a concentration of 1-10 mM.

In an article in *Biochim. Biophys. Acta* (BBA) (In Press, 1976) by the present investigating team, a general study on fusion taking into account the operability of $Ca^{2+}$ as versus other divalent metals especially magnesium is undertaken and there appears to be a "threshold" concentration at which $Ca^2$ becomes effective in inducing membrane fusion and gives for phosphatidylserine membranes a threshold concentration of 1 mM for $Ca^{2+}$. For this invention, the range for addition of $Ca^{2+}$ is 1-10 mM. There is also a finding that phosphatidylserine is considerably more sensitive to fusion by $Ca^{2+}$ and in effect for the present experimental $Ca^{2+}$ is much preferred to $Mg^{2+}$ which has disadvantages as to operativeness.

Figure 1:
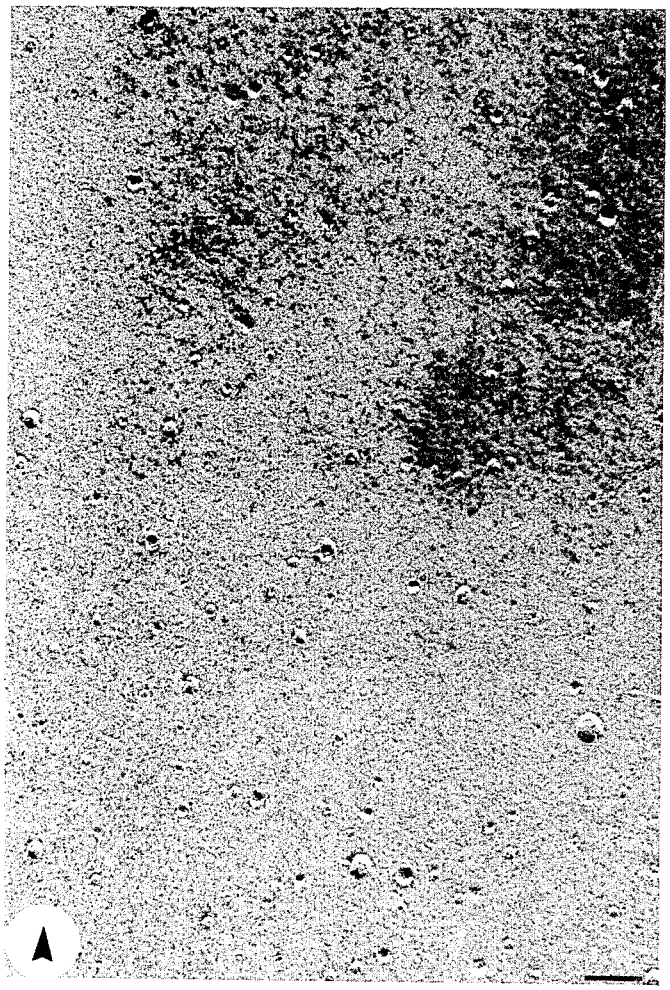
FIG. 1 shows the small unilamellar vesicle particles.
Figure 2:
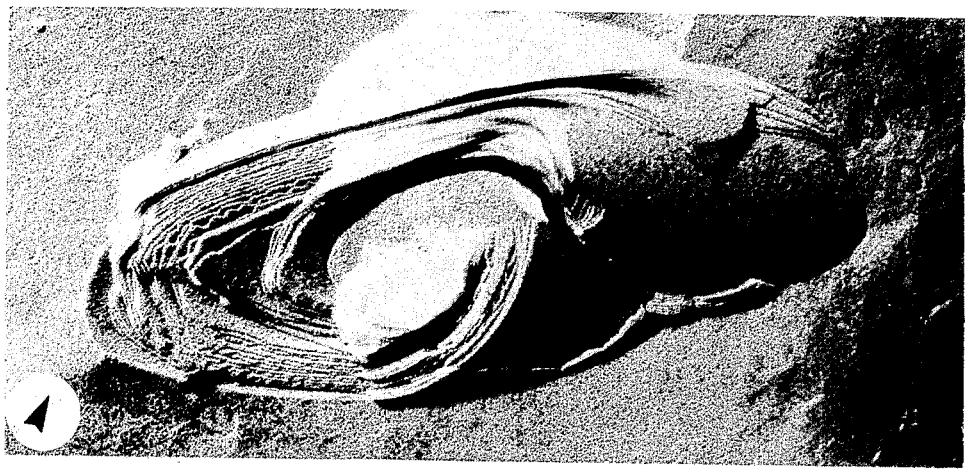
FIG. 2 shows the intermediate cochleate shape.

Calcium chloride was added (10 mM per ml for one hour at 37° C). Structures were produced and of these many resembled cochleate cylinders. See FIG. 2.

Figure 3:
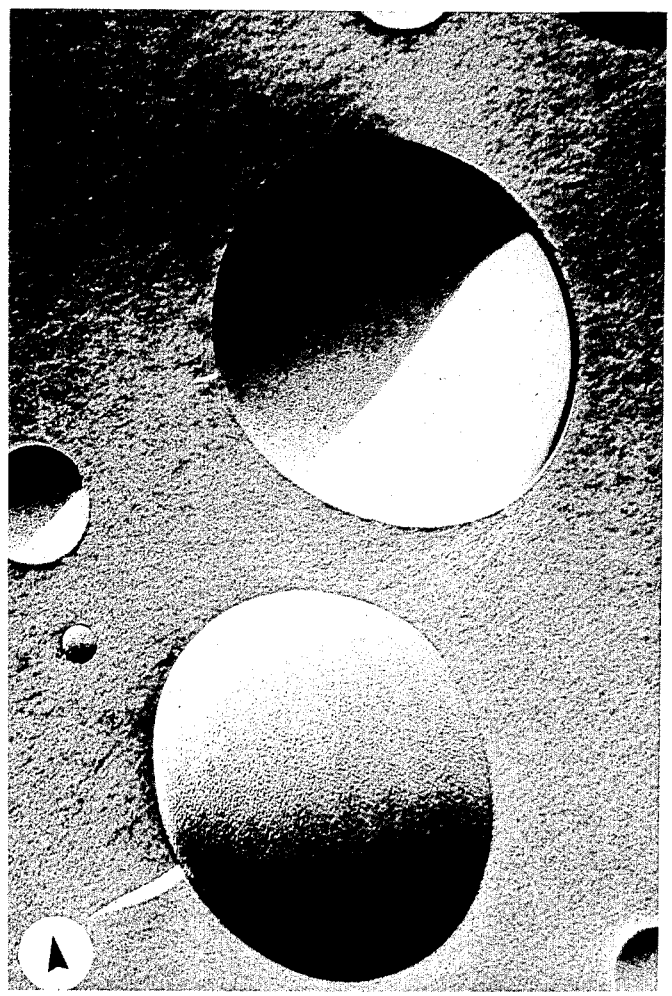
FIG. 3 shows the large unilamellar vesicle particles.
Figure 4:
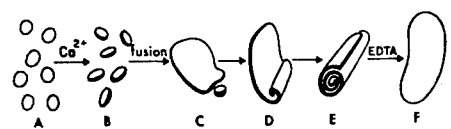
FIG. 4 is a schematic of the process and products of the invention, giving a schematic representation of the effect of $Ca^{2+}$ on sonicated phosphatidylserine vesicles leading to the formation of cochleate cylinders. A: sonicated vesicles in NaCl buffer before addition of $Ca^{2+}$, shown as spheroidal particles with an aqueous interior and a single lipid bilayer shell. B, C, and D are suggested intermediate steps involving the aggregation and fusion of the spheroidal vesicles into cochleate cylinders. B represents the step in which $Ca^{2+}$ ruptures the vesicles forming flat bilayer disks. C indicates fusion of the disks into large sheets in order to minimize hydrocarbon-water contact. D indicates the beginning of the folding of the flat sheet into a cylinder. E: cochleate cylinders forming by spiral folding of the continuous planar membrane sheets shown in C and D. F: large unilamellar vesicles created by unfolding of the cochleate spiral membranes following incubation with EDTA.

Finally, on addition of EDTA (15 mM), a calcium chelating agent, to the preparation, there was produced large unilamellar vesicles (LUV). See FIG. 3. These large vesicles exhibited a diameter in the range of 2,000-12,000 A and apparently were created by fusion of smaller unilamellar vesicles (SUV). These LUV particles are large closed spherical unilamellar vesicles.

ENTRAPPMENT OF DRUGS

Post the sonication treatment above, it has been possible to introduce drugs which are entrapped and made a part of the final product. Such a use of lipid vesicles as carriers to introduce a drug as Actinomyin D into resistant tumor cells has been described in a paper by members of the present team of investigators and entitled "Use of Lipid Vesicles as Carriers to Introduce Actinomycin D into Resistant Tumor Cells," by D. Papahadjopoulos, G. Poste, W. J. Vail, and June L. Beidler, *Cancer Research,* In Press, 1976; and also "Drug Containing Lipid Vesicles Render Drug Resistant Tumor Cells Sensitive to Actinomycin D," by Poste and Papahadjopoulos, *Nature,* In Press, 1976. Also relative to the polynucleotide Poly I Poly C (submitted for publication 1976) is the following title, "Cellular Uptake and Protection Against Virus Infection by Poly I Poly C Entrapped Within Phospholipid Vesicles," by E. Mayhew, D. Papahadjopoulos et al.

Illustrative of additional drugs which have been encapsulated in the phosphatidylserine vesicles are cyclic 3',5'-adenosine monophosphate (cyclic AMP) and also dibutyryl-cyclic AMP, RNA, DNA, and arabinose cytocine and its phosphorylated analogs.

In this process it is noted that if phosphatidylserine is utilized with $Ca^{2+}$, there is produced an intermediate cochleate structure which further produces a large unilamellar vesicle by fusion as a final product from small unilamellar vesicles. It is believed that the addition of $Ca^{2+}$ to the sonicated phosphatidylserine vesicles induces a large increase in permeability with loss of $Ca^+$ and $Cl^-$ indicating rupture of the vesicles with loss of the initially captured ions and water. The resulting membranes contain phosphatidylserine and $Ca^{2+}$ at a 2:1 molar ratio and the phospholipid aliphatic acyl chains are in a crystalline state. It has been shown previously that this rupture of phosphatidylserine membrane is caused by the presence of $Ca^{2+}$ only on one side of the membrane possibly as a result of asymmetry in the membrane surface charge. The instability caused by "crystallization" of the outer monolayer may be responsible for rupturing of the vesicles and their subsequent fashion.

It is further postulated that the collapsed small vesicles fuse into large planar sheets which then coil about an initial point of folding to form cochleate cylinders. In this case the $Ca^{2+}$ acts both to crystallize the individual lamellae and to produce a tightly folded multilamallar system with a 54 A repeat distance. This repeat distance is smaller than in other multilamellar lipid systems such as phosphatidylcholine dispersed in 0.1 molar aqueous KCl and indicates an interlamellar attraction which is believed to promote the spiral formation.

The addition of EDTA to cochleate cylinders chelates $Ca^{2+}$, restoring negative charge and normal fluidity to the membranes. This process is believed to involve first the unfolding of the bilayers of the cochleate cylinders into planar sheets which seal by fusion at the edges which form very large closed unilamellar vesicles.

The present invention indicates that formation of large unilamellar vesicles can be accomplished by removing $Ca^{2+}$ from cochleate cylinders using a calcium chelating agent such as EDTA or EGTA.

The advantage of the large unilamellar vesicles (LUV) product for phosphatidylserine over the smaller variety (SUV) lies in the greater area of aqueous space in the encapsulating area. The large unilamellar vesicles contain large aqueous spaces and are of large diameters (2,000-12,000 A) which encapsulate even very large macromolecular examples such as whose viruses.

A general advantage in using vesicles is that it is known that lipid vesicles with similar composition to those presently described have been known to fuse with the plasma membrane of living cultured cells. It is believed that the contents will be transferred into the cytoplasma of the recepient cells bypassing both the lysomal apparatus and the permeable barrier of the cell.

EXAMPLE 1

Phosphatidylserine purified from bovine brain was utilized as a starting material. This phospholipid was suspended in aqueous buffer solution containing 100 mM NaCl at pH 7.4 and exposed to ultrasonic radiation in a closed system under nitrogen. The small unilamellar vesicles (SUV) formed by the above procedure were incubated with calcium chloride which is here added to the solution to a full concentration of 1-10 mM (1 hour at 37° C). An alternative procedure was to dialyze the vesicles against 1 mM calcium chloride in the original buffer (12 hours at 24° C). This procedure resulted in spirally folded cochleated cylinders much larger than the original sonicated vesicles. These cochleated structures were concentrated by centrifugation (10,000 × g × 10 mins.) and were mixed with a concentrated solution of the material to be encapsulated such as Poly I Poly C, RNA, DNA, Actinomycin D, cyclic 3'5'-adenosine monophosphate, and arabinose cytocine and its phosphorylated analogs. Ethylene diamine tetraacetate sodium salt (EDTA) was then added in slight molar excess of the $Ca^{2+}$ present. The suspension was adjusted to pH 7.4 with sodium hydroxide, shaken vigorously 10 minutes at 37° C, and finally equilibrated for another 30 minutes at that same temperature. This procedure resulted in large closed spherical unilamellar vesicles. A significant percentage of the macromolecular drugs present (2–20%, depending on the amount of lipid and volume of the reaction) was captured within these vesicles. The non-incorporated material was removed by repeated centrifugation (48,000 × g × 20 min., 20° C) and resuspended in the original buffer or regular phosphate buffered saline.

EXAMPLE 2

In a similar procedure as shown in Example 1 utilizing as a starting material an equimolar mixture of phosphatidylserine with cholesterol, a change was made in the cochleating agent. In this case, a higher concentration of $CaCl_2$ (2–3 mM) was needed in the formation of the cochleate cylinders. Alternatively the formation of the large unilamellar vesicles was achieved by dialysis against buffer containing 20 mM EDTA.

I claim:

1. A method for preparing large unilamellar phosphatidylserine vesicles with diameters of about 2,000–12,000 A which comprises:
   (1) subjecting a solution of phosphatidylserine in aqueous NaCl buffer to ultrasound treatment to give a sonicated preparation of said phosphatidylserine containing small spheroidal vesicals in the range of 200–500 A diameter;
   (2) adding $Ca^{2+}$ in the amount of 1–10 mM and incubating for about 30 minutes to 1 hour at room temperature above 10° C to produce large multilamellar structures, a substantial portion of which are cochleate cylinders;
   (3) adding a chelating agent for $Ca^{2+}$ at a pH of about 7.4 in an amount sufficient to chelate surplus calcium to produce the desired large closed spherical unilamellar phosphatidylserine vesicles.

2. The method of claim 1 wherein the addition of $Ca^{2+}$ is made by $CaCl_2$.

3. The method of claim 1 wherein the chelating agent is selected from a member of the group consisting of EDTA and EGTA.

4. The method of claim 1 wherein in step 2 the incubation is carried out for about 1 hour at 37° C.

5. A large unilamellar phosphatidylserine vesicle product produced according to the method of claim 1.

6. A method of preparing large unilamellar phosphatidylserine vesicles with diameter of about 2,000–12,000 A containing an encapsulated drug and which method comprises:
   (1) subjecting a solution of phosphatidylserine in aqueous NaCl buffer to ultrasound treatment to give a sonicated preparation of said phosphatidylserine containing small spheroidal vesicles in the range of 200–500 A diameter;
   (2) adding an effective amount of a drug to the solution of phosphatidylserine for encapsulation;
   (3) adding $Ca^{2+}$ in the amount of 1–10 mM and incubating for about 30 minutes to 1 hour at room temperature above 10° C to produce large multilamellar structures, a substantial portion of which are cochleate cylinders;
   (4) adding a chelating agent for $Ca^{2+}$ at a pH of about 7.4 in an amount sufficient to chelate surplus calcium to produce the desired large closed spherical unilamellar phosphatidylserine vesicles.

7. The method of claim 6 wherein the addition of $Ca^{2+}$ is made by $CaCl_2$.

8. The method of claim 6 wherein the chelating agent is selected from a member of the group consisting of EDTA and EGTA.

9. The method of claim 6 wherein in step 3 the incubation is carried out for about 1 hour at 37° C.

10. The method of claim 6 wherein the drug encapsulated is selected from one member of a group consisting of Actinomycin D, cyclic 3'5'-adenosine monophosphate, Poly I Poly C, RNA, DNA, and arabinose cytocine and its phosphorylated analogs.

11. The method of claim 10 wherein the drug encapsulated is Actinomycin D.

12. The method of claim 10 wherein the drum encapsulated is cyclic 3'5'-adenosine monophosphate.

13. The method of claim 10 wherein the drug encapsulated is Poly I Poly C.

14. The method of claim 10 wherein the drug encapsulated is RNA.

15. The method of claim 10 wherein the drug encapsulated is DNA.

16. The method of claim 10 wherein the drug encapsulated is arabinose cytocin and its phosphorylated analogs.

17. A large unilamellar phosphatidylserine vesicle product produced according to the method of claim 6.